(12) United States Patent
Bernhardt

(10) Patent No.: US 9,017,420 B1
(45) Date of Patent: Apr. 28, 2015

(54) INFLATABLE INTERFACE FOR USE BETWEEN A LIMB LINER AND A LIMB PROSTHESIS

(76) Inventor: Frederick S. Bernhardt, Croydon, PA (US)

(*) Notice: Subject to any disclaimer, the term of this patent is extended or adjusted under 35 U.S.C. 154(b) by 757 days.

(21) Appl. No.: 12/684,789

(22) Filed: Jan. 8, 2010

(51) Int. Cl.
  *A61F 2/80* (2006.01)
  *A61F 2/78* (2006.01)
  *A61F 2/28* (2006.01)

(52) U.S. Cl.
  CPC .................................... *A61F 2/2814* (2013.01)

(58) Field of Classification Search
  CPC ...................................... A61F 2/7843
  USPC ...................................... 623/33–37
  See application file for complete search history.

(56) References Cited

U.S. PATENT DOCUMENTS

| | | | | |
|---|---|---|---|---|
| 3,889,301 A | * | 6/1975 | Bonner, Sr. | 623/37 |
| 5,156,629 A | | 10/1992 | Shane et al. | |
| 5,314,497 A | * | 5/1994 | Fay et al. | 623/34 |
| 5,387,245 A | | 2/1995 | Fay et al. | |
| 5,464,443 A | * | 11/1995 | Wilson et al. | 623/37 |
| 5,549,709 A | * | 8/1996 | Caspers | 623/24 |
| 5,724,714 A | * | 3/1998 | Love | 29/458 |
| 5,735,906 A | * | 4/1998 | Caspers | 623/34 |
| 5,746,772 A | * | 5/1998 | Jacobs | 623/35 |
| 5,904,722 A | * | 5/1999 | Caspers | 623/34 |
| 6,149,691 A | * | 11/2000 | Fay et al. | 623/37 |
| 6,508,842 B1 | * | 1/2003 | Caspers | 623/32 |
| 6,554,868 B1 | * | 4/2003 | Caspers | 623/34 |
| 7,670,386 B2 | * | 3/2010 | Ezenwa | 623/37 |
| 2002/0087215 A1 | * | 7/2002 | Caspers | 623/34 |
| 2002/0088384 A1 | * | 7/2002 | Bernhardt | 112/475.12 |
| 2003/0078674 A1 | | 4/2003 | Phillips | |
| 2003/0181990 A1 | | 9/2003 | Phillips | |
| 2004/0098136 A1 | * | 5/2004 | Caspers | 623/34 |
| 2004/0143345 A1 | * | 7/2004 | Caspers | 623/36 |
| 2008/0147204 A1 | * | 6/2008 | Ezenwa | 623/33 |
| 2010/0070051 A1 | * | 3/2010 | Carstens | 623/34 |
| 2013/0123940 A1 | * | 5/2013 | Hurley et al. | 623/33 |

* cited by examiner

*Primary Examiner* — Jacqueline Woznicki
(74) *Attorney, Agent, or Firm* — LaMorte & Associates, P.C.

(57) ABSTRACT

An interface for use between the socket of a prosthesis and a limb liner. The interface has a double-layered body having a bottom end and an open top end. A mounting pinhole can be formed through the bottom end so that a connector pin on the limb liner can extend through the interface and engage the prosthesis. Alternatively, the bottom end can be formed without a pinhole to accommodate a non-locking type liner. The interface has an interior layer, an exterior layer and an interposed gap space. A vent is provided for selectively controlling airflow into and out of the gap space. The gap space can be inflated in one of two ways. First, the gap space can be made self-inflating by placing open cell foam material into the gap space. Second, a manual pump can be attached to the interface that actively pumps air into the gap space.

11 Claims, 5 Drawing Sheets

INFLATABLE INTERFACE FOR USE BETWEEN A LIMB LINER AND A LIMB PROSTHESIS

BACKGROUND OF THE INVENTION

1. Field of the Invention

In general, the present invention relates to inflatable liners that are used between a partially amputated limb and a limb prosthesis. More, particularly, the present invention relates to the structure of a liner, its inflation mechanisms and its interaction with both the amputated limb and the limb prosthesis.

2. Prior Art Description

Many people who have amputated limbs or partially amputated limbs rely upon prosthetics to live more active lives. When a person is fitted for a limb prosthesis, that person may be fitted with a limb liner. A limb liner is typically worn over the portion of the limb that remains on the body. A limb liner is an elastomeric device that is pulled over the residual limb. The liner conforms to the shape of the residual limb and creates a strong frictional attachment to the skin of the residual limb. In many instances, a metal locking pin extends from the tip of the limb liner. The locking pin is used to engage the prosthetic limb when a prosthetic limb is mated with the limb liner. As such, the limb liner acts as the anchor for retaining the limb prosthesis onto the residual limb.

When a limb prosthesis is manufactured, a cast is taken of the limb liner while the limb liner is being worn. The cast is used to produce a socket. The socket is then attached to the limb prosthesis. The socket of the limb prosthesis is the portion of the prosthesis that mates with the limb liner and conforms to the shape of the limb liner and the underlying residual limb. In this manner, the limb prosthesis will properly fit onto the limb liner and residual limb.

Amputees commonly retain their prosthetic limbs for many years. However, during this time, the amputee may gain weight, lose weight, lose muscle mass, or otherwise undergo physiological changes. Furthermore, amputees may retain water, have limb swelling or undergo other physical changes that can cause the size of the amputated residual limb to vary. As the residual limb changes in size and/or contour, the configuration of the limb liner also changes. As a result, the shape of the limb liner may no longer match the shape of the socket in the prosthetic limb. This mismatch in shape creates gaps between the limb liner and the socket of the prosthesis. The gaps can cause the prosthesis to feel loose in certain places and overly tight in others. Furthermore, the gaps can cause physical discomfort by causing chafing against the residual limb.

In the prior art, fabric-based liner socks have been used to compensate for any inconsistencies between the configuration of the limb liner and the configuration of the limb prosthesis. Prior art liner socks are basically knitted or woven socks that are worn over the limb liner. The liner sock becomes compressed at points of contact between the limb liner and the limb prosthesis. The liner sock is less compressed in areas of gaps. Accordingly, the liner sock helps to fill the gaps between the limb liner and the prosthesis.

The ability of a knitted or woven sock to fill a gap is limited to gaps that are typically less than $\frac{1}{32}^{nd}$ of an inch wide. In situations where larger gaps are commonplace, amputees typically turn to a gel liner or multiple layers of knitted socks. Gel liners are socks molded from an elastomeric material. These gel liners are worn around the limb liner when the limb liner is inserted into the socket of the prosthesis. The problem associated with such gel liners is one of compromise. The socket of the prosthesis is created from a mold of the limb liner. Accordingly, these two elements tend to be very close in shape. If the amputee's residual limb undergoes some physiological change, then that change may be localized. That is, only certain segments of the amputee's residual limb change, while the majority remains relatively the same. When a gel liner or multiple socks are used, the padding adds thickness to the entire limb liner. Accordingly, the segments of the limb liner that fit properly are now tight. In many situations, the discomfort created by a gel liner outweighs its benefits. Accordingly, gel liners are made thin, but not too thin so as not to be able to fill a gap. This compromise often makes gel liners either too loose or too tight, or both in separate areas.

The disadvantages of a gel liner can be avoided by the use of an inflatable liner. In the prior art, several inflatable liners have been invented for use between amputated limbs and prostheses. The inflatable liners can be selectively inflated to provide an adjustable interface between the residual limb and the prosthesis. However, prior art inflatable liners typically embody at least one of two major disadvantages. The disadvantages are either that the bladder is built into the socket of the prosthesis or that the bladder is used in place of a traditional limb liner.

In both U.S. Patent App. Pub. 2003/0078674, to Phillips, entitled Socket Insert Having A Bladder System, and U.S. Patent App. Pub. 2003/0181990, to Phillips, entitled Socket Insert Having A Bladder System, an inflatable bladder system is shown where the inflatable bladder is formed as part of the prosthetic's socket. These references provide bladders in only some parts of the socket. Accordingly, there is no guarantee that the bladders will fill any gaps that may exist between the amputee's limb and the sock. Furthermore, the bladder system is built into the structure of the prosthetic socket. The socket is custom made for each amputee and is both expensive and time consuming to manufacture. Adding bladders to this structure significantly increases the cost and labor of manufacture, thereby making this expensive component more expensive while significantly decreasing the reliability and life expectancy of the socket.

In U.S. Pat. No. 5,156,629 to Shane, entitled Pneumatic Prosthetic Insert, and U.S. Pat. No. 5,387,245 to Fay, entitled Inflatable Prosthetic Liners, inflatable limb liners are disclosed. These inflatable limb liners are designed to take the place of the elastomeric limb liner around which the socket of the prosthesis is molded. By eliminating the elastomeric limb liner, room is made for the inflatable limb liner.

As will be understood among amputees, residual limbs vary widely in shape and contour from patient to patient. This is why the socket of a prosthesis is custom molded to a limb liner. By replacing the limb liner with a single-sized inflatable liner, it would be impossible to create a quality interconnection between the residual limb and prosthetic socket of most amputees. Furthermore, inflatable limb liners lack the physical structure to support a connector pin. The connector pin creates the strongest mechanical interconnection between the limb liner and the prosthetic limb. Without a connector pin, many amputees would not be able to keep the prosthetic limb attached to their bodies during normal everyday activities.

A need therefore exists for a new type of inflatable interface that is designed to lay between an ordinary prosthetic limb socket and an ordinary limb liner having a connector pin. A need also exists for an inflatable interface that is very thin so as not to make the limb liner feel tight in well-fitted areas. However, the inflatable interface can be selectively inflated to fill significant gaps that may be encountered between the limb liner and the prosthetic limb socket. Lastly, a need exists for an inflatable interface where the limb liner has no adverse effect upon the ability of the limb liner pin to interconnect with the limb prosthesis. These needs are all met by the present invention as described and claimed below.

SUMMARY OF THE INVENTION

Amputees often wear a prosthesis with a socket shaped to conform to a limb liner that is worn on a residual limb. The limb liner has a connection pin that selectively interconnects with the socket. The present invention is a system and method of providing an interface between the socket of the prosthesis and the limb liner to eliminate any gaps that may cause unintentional movement of the prosthesis. The interface includes a double-layered body having a bottom end and an open top end. A mounting pin hole is formed through the bottom end so that the connector pin on the limb liner can extend through the interface and engage the prosthesis.

The interface has an interior layer, an exterior layer and a gap space interposed between the interior layer and the exterior layer. Both the interior layer and the exterior layer are made of air-impervious material. A vent is provided for selectively controlling airflow into and out of the gap space. The gap space can be inflated in one of two ways. First, the gap space can be made self-inflating by placing open cell foam material into the gap space. The open cell foam material biases the gap space open and draws air into the gap space through the vent. Second, a manual pump can be attached to the interface that actively pumps air into the gap space.

BRIEF DESCRIPTION OF THE DRAWINGS

For a better understanding of the present invention, reference is made to the following description of exemplary embodiments thereof, considered in conjunction with the accompanying drawings, in which.

DETAILED DESCRIPTION OF THE DRAWINGS

Although the present invention interface can be embodied for use with an arm prosthesis or a transfemoral leg prosthesis, the embodiment illustrated shows the interface being used on a transtibial leg prosthesis. This embodiment is selected in order to set forth the best mode contemplated for the invention. The illustrated embodiment, however, is merely exemplary and should not be considered a limitation when interpreting the scope of the appended claims.

Figure 1:
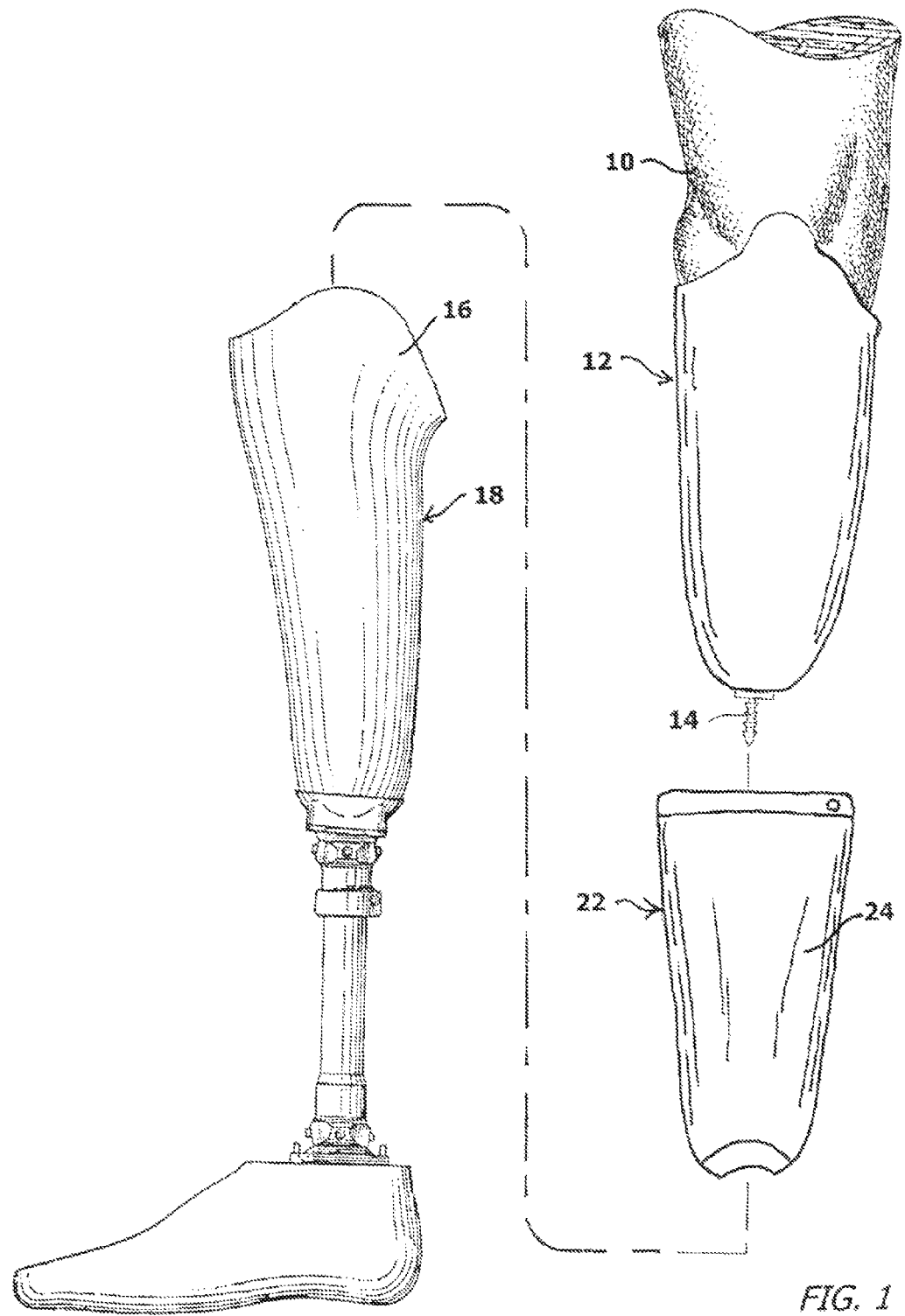
FIG. 1 is a perspective view of an amputee's prosthesis mounting system that includes a limb liner, prosthesis socket and interface.
Figure 2:
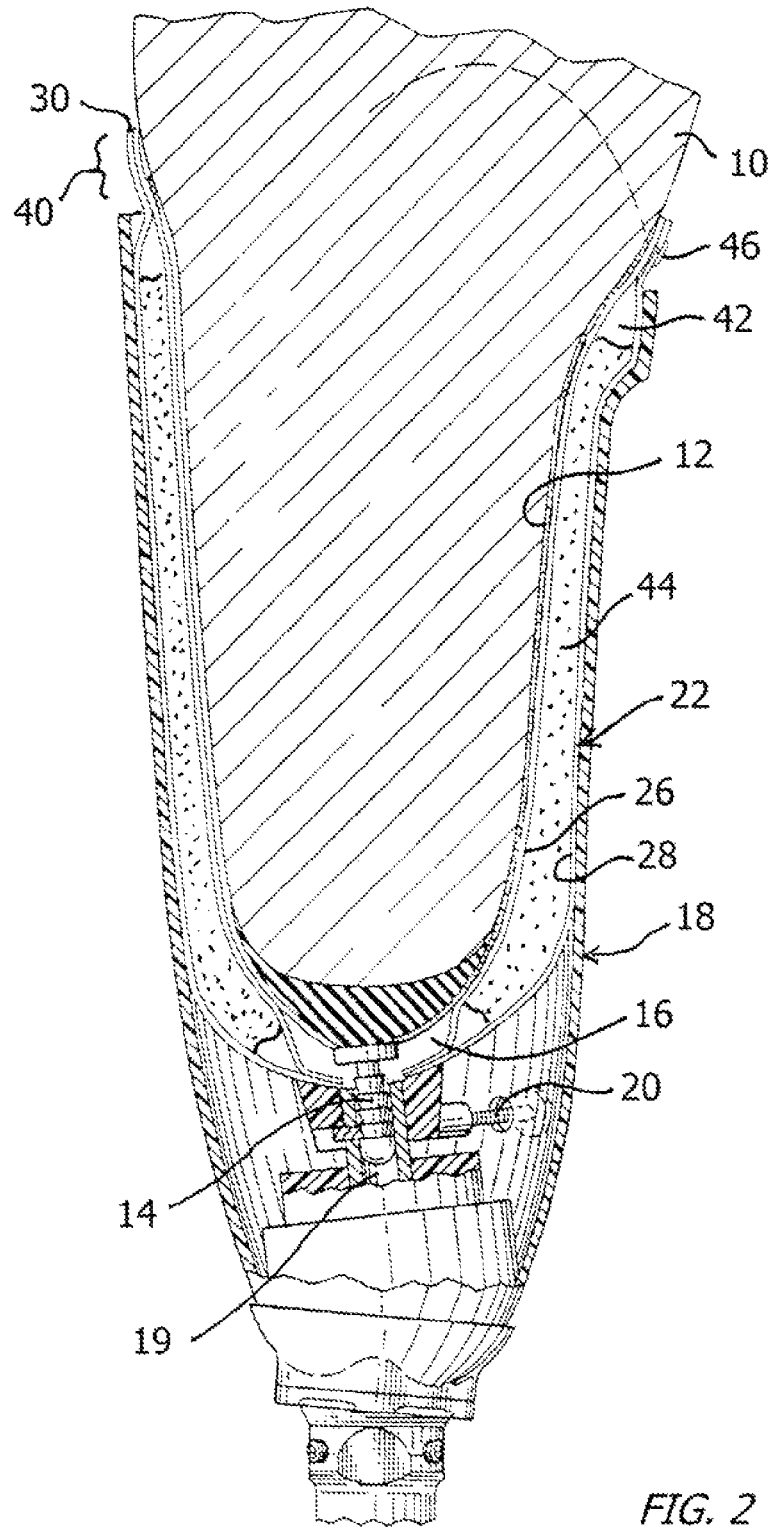
FIG. 2 is a selectively cross-sectioned view of the embodiment of FIG. 1 shown in an assembled condition.

Referring to FIG. 1 and FIG. 2, a residual limb 10 of an amputee is shown. The residual limb 10 is fitted with an elastomeric limb liner 12 using traditional fitting techniques. The limb liner 12 covers the residual limb 10. A connector pin 14 extends from the bottom of the limb liner 12. The connector pin 14 is used to interconnect the limb liner 12 with the socket 16 of a limb prosthesis 18.

The limb prosthesis 18 can have many shapes, depending upon the manufacturer's model and the needs of the amputee. The limb prosthesis 18 includes a socket 16 for receiving the amputee's residual limb 10 surrounded by the limb liner 12. Typically, the socket 16 is fabricated by taking a mold of the amputee's residual limb 10 while wearing a limb liner 12. Accordingly, the socket 16 has an internal shape that is nearly identical to the external shape of the limb liner 12, while worn on the residual limb 10. A receptacle 19 is formed in the bottom of the socket 16. The receptacle 19 receives the connector pin 14 on the limb liner 12. An engagement mechanism 20 is present on the exterior of the prosthesis 18 that enables the wearer to selectively lock and unlock the connector pin 14 of the limb liner 12 to the prosthesis 18.

A socket/limb liner interface 22 is provided. The purpose of the interface 22 is to compensate for any gaps that may form between the socket 16 of the prosthesis 18 and the limb liner 12 so that the limb liner 12 always feels secure within the socket 16 when worn.

Figure 3:
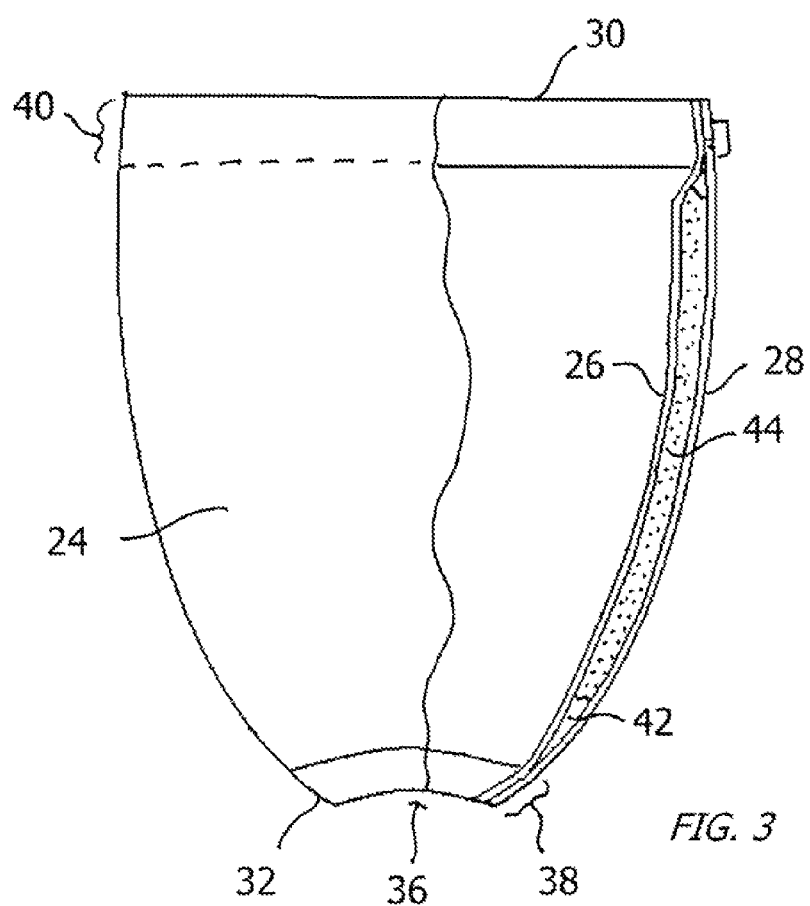
FIG. 3 shows a cross-sectional view of an exemplary embodiment of an interface.

Referring to FIG. 3, in conjunction with both FIG. 1 and FIG. 2 it can be seen that the body 24 of the interface 22 is double layered. That is, the body 24 of the interface is made from two layers of material that lay atop each other. The two layers include an interior layer 26 and an exterior layer 28. Both the interior layer 26 and the exterior layer 28 are made from material that is impervious to air.

The body 24 of the interface 22 is generally cup-shaped to match the external shape of the limb liner 12 and the internal shape of the prosthetic's socket 16. The body 24 of the interface 22 has an open top end 30 and a mostly closed bottom end 32. A continuous peripheral wall 34 extends between the bottom end 32 and the top end 30.

A hole 36 is formed through the center of the bottom end 32 of the interface 22. The hole 36 has a diameter just slightly larger than that of the connector pin 14 that extends from the limb liner 12. The interior layer 26 and the exterior layer 28 of the interface 22 are joined together in an area 38 immediately surrounding the hole 36. As such, there is no gap between the interior layer 26 and the exterior layer 28 within this area 38. The gapless area 38 is preferably circular in shape and extends in a concentric circle around the hole 36, having a diameter preferably between one inch and three inches.

In the gapless area 38, no inflation between the interior layer 26 and exterior layer 28 can occur. Accordingly, the interface 22 always lays flat in the gapless area 38. This prevents the interface from separating the limb liner 12 from the bottom of the socket 16, thus preventing the connector pin 14 from properly locking in place.

The interior layer 26 and the exterior layer 28 of the interface 22 are also joined together in a predetermined area 40 leading to the open top end 30 of the interface body 24. In this predetermined area 40, there is no inflatable gap between the interior layer 26 and the exterior layer 28. The predetermined area 40 extends at least one inch below the brim of the open top end 30.

Between the gapless area 38 at the bottom of the interface 22 and the gapless area 40 at the top end of the interface 22 is an inflatable gap 42. Within the inflatable gap 42, the interior layer 26 and the exterior layer 28 are not continuously joined together, thereby enabling the gap 42 to selectively expand and contract depending upon the air pressure within the gap 42. The gap 42 may be empty. However, in the illustrated embodiment, a layer of open cell foam 44 is interposed between the interior layer 26 and the exterior layer 28. The layer of open cell foam 44 has a preferred thickness of between $1/8^{th}$ and $1/2$ of an inch when fully aerated. However, when compressed, the layer of open cell foam 44 can easily reduce to a thickness of less than $1/32^{nd}$ of an inch.

Figure 4:
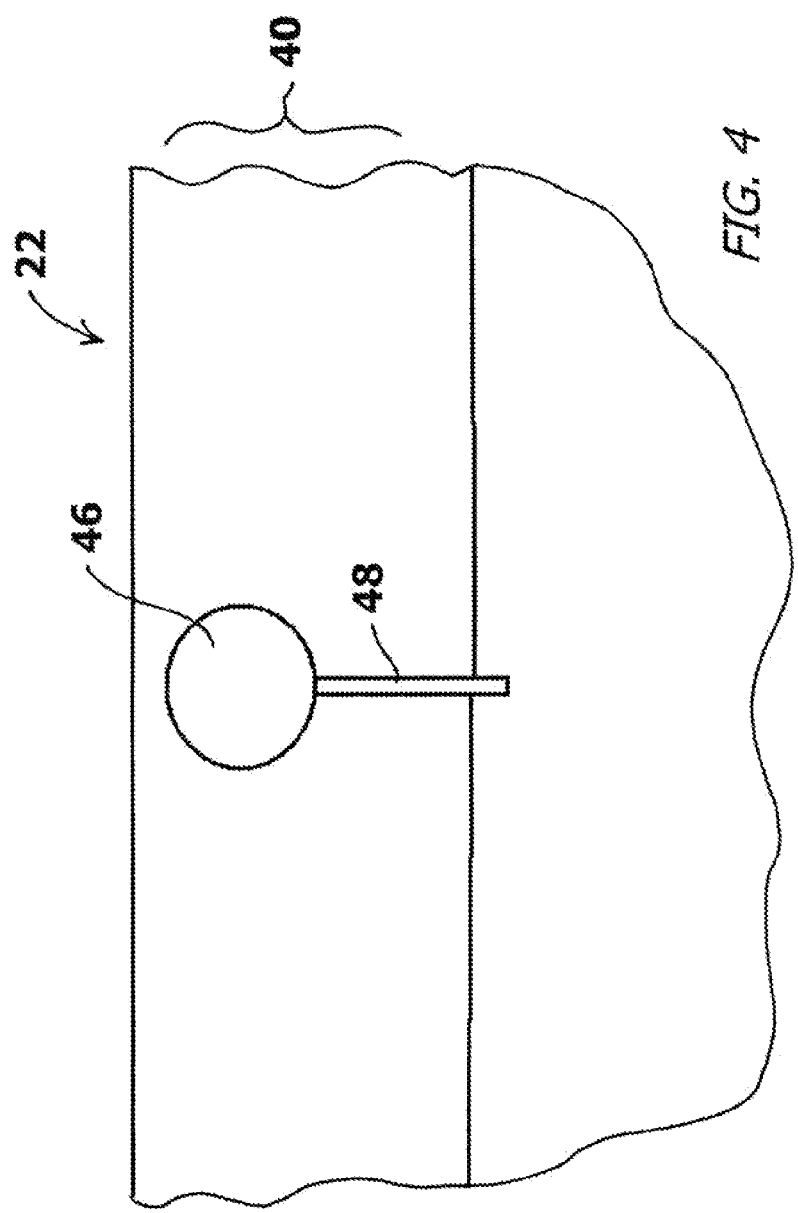
FIG. 4 shows an enlarged view of a segment of the exemplary interface.

Referring to FIG. 4 with FIG. 3, it can be seen that a manually operated vent 46 is provided. The vent 46 is normally closed, but can be opened by being pressed, turned or otherwise manually manipulated. The vent 46 is disposed in the gapless area 40 near the open top of the interface 22. A conduit 48 is provided that interconnects the vent 46 to the gap 42 containing the open cell foam 44.

Referring in unison to FIGS. 1-4, it will be understood that in order to use the interface, an amputee places a limb liner 12 over his/her residual limb 10. Prior to inserting the limb liner 12 into the socket 16 of the prosthesis 18, the interface 22 is pulled over the limb liner 12. The connector pin 14 at the bottom of the limb liner 12 is advanced through the hole 36 in the bottom end 32 of the interface 22.

Prior to inserting the limb liner 12 and the interface 22 into the socket 16 of the prosthesis 18, the vent 46 is opened. With the vent 46 opened, both the limb liner 12 and interface 22 are advanced into the socket 16. The insertion of the interface 22 into the socket 16 causes part of the interface 22 to compress. As the gap 42 within the interface 22 compresses, the open cell foam 44 compresses and air is displaced out of the vent 46.

Once the limb liner 12 and surrounding interface 22 are fully seated into the socket 16, the vent 46 is held open for a short period of time. This enables air to flow back into the gap 42. With an abundance of available air, the open cell foam 44 will expand in any area where it is not compressed. As the open cell foam 44 expands, it spreads the interface 22 in any non-compressed area. The interface 22, therefore, automatically expands to fill any gap space that may exist between the limb liner 12 and the socket 16. Once the vent 46 is closed, air becomes trapped within the interface 22, thereby retaining the interface 22 in a configuration that uniquely fills the gap spaces between the limb liner 12 and the socket 16.

If an amputee feels as though the socket 16 of the prosthesis 18 has become too tight, the amputee need only transfer more of his/her weight to the prosthesis 18 and open the vent 46. This will displace more air out of the interface 22, thereby making the interface 22 thinner and the fit of the limb liner 12 looser.

If an amputee feels as though the socket 16 of the prosthesis 18 has become too loose, the amputee need only transfer less of his/her weight to the prosthesis 18 and open the vent 46. This will enable the open cell foam 44 to expand and fill any existing gap spaces, thereby making the interface 22 thicker and the fit of the limb liner 12 tighter.

Figure 5:
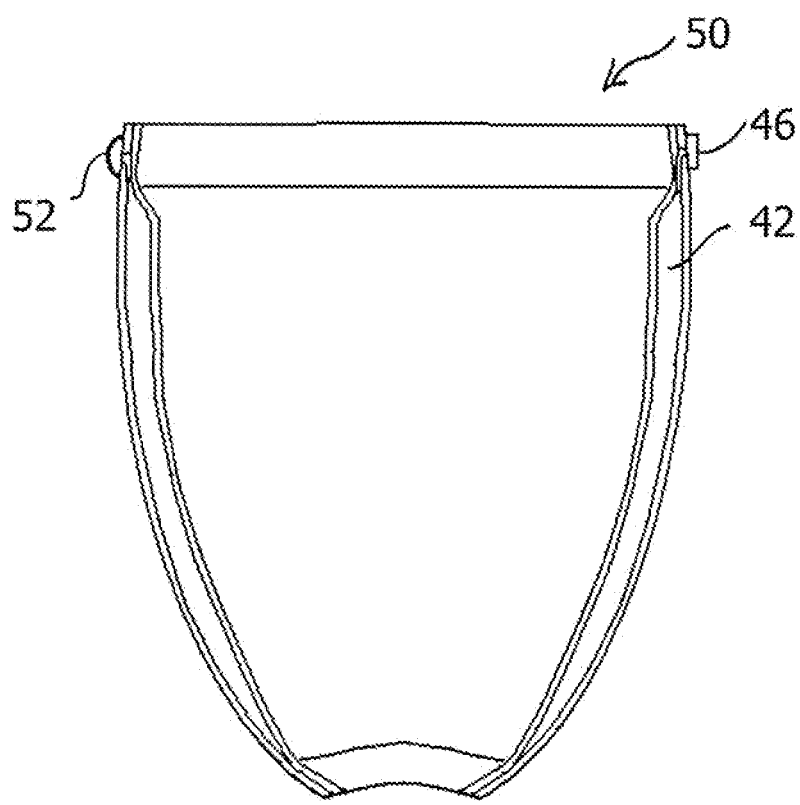
FIG. 5 is a front view of an alternate embodiment of an interface.

Referring to FIG. 5, an alternate embodiment of a limb liner/socket interface 50 is shown. The embodiment is a slight modification of the embodiment previously described and like number will be used to identify like parts to avoid confusion.

In the embodiment of FIG. 5, a manual air pump 52 is provided. When depressed, the manual air pump 52 forces air into the gap 42 within the interface 50. The use of the air pump 52 eliminates the need for the open cell foam. Accordingly, to add air into the gap 42 of the interface 50, the manual air pump 52 is pressed. To remove air from the gap 42, the vent 46 is opened. By selectively controlling the amount of air in the gap 42, the fit around the limb liner 12 can be made more or less snug.

It will be understood that the embodiments of the present invention that are illustrated and described are merely exemplary and that a person skilled in the art can make many variations to those embodiments. For instance, the shape of the interface can vary widely to accommodate many different types of amputee limbs. Furthermore, many vent controls and miniature manual air pumps exist in the prior art. Many of those designs can be adapted for use by the present invention. All such embodiments are intended to be included within the scope of the present invention as defined by the claims.

What is claimed is:

1. An interface for filling gaps that form between a limb liner and a socket of a prosthetic limb, said interface comprising:
    a double-layered body having a bottom end and an open top end, wherein a mounting pin hole is disposed through said bottom end;
    said body having an interior layer and an exterior layer wherein said interior layer is connected to said exterior layer in a first predetermined area surrounding the mounting pin hole, said first predetermined area being a concentric circle surrounding said hole where the interior layer lays flush against said exterior layer,
    and wherein said interior layer is connected to said exterior layer in a second predetermined area proximate said open top end;
    a gap space separating said interior layer and said exterior layer within said body at all points between the first predetermined area and second predetermined area, so that the first predetermined area and second predetermined area are of a lesser thickness than the body at all points between the first predetermined area and second predetermined area,
    wherein both said interior layer and said exterior layer are made of air-impervious material; and
    a vent for selectively controlling air flow into and out of said gap space.

2. The interface according to claim 1, wherein said concentric circle has a diameter between one quarter of an inch and three inches.

3. The interface according to claim 1, wherein said second predetermined area extends at least one quarter of an inch from said open top end.

4. The interface according to claim 3, wherein said vent is disposed in said second predetermined area.

5. The interface according to claim 4, further including a conduit formed through said second predetermined area that connects said vent to said gap space.

6. The interface according to claim 1, further including open cell foam material disposed in said gap space.

7. The interface according to claim 6, wherein said open cell foam material varies in thickness at different points in said gap space.

8. The interface according to claim 1, further including a pump for actively adding air to said gap space.

9. A self-inflating interface to be worn between a limb liner and a socket of a prosthetic limb, said interface comprising:
    a double-layered body having a bottom end and an open top end;
    said body having an interior layer and an exterior layer wherein said interior layer is connected to said exterior layer in a first predetermined area proximate said bottom end, said first predetermined area being a circular area where said interior layer lays flush against said exterior layer, and wherein said interior layer is connected to said exterior layer in a second predetermined area proximate said open top end;
    a gap space separating said interior layer and said exterior layer within said body at all points between said first predetermined area and second predetermined area, so that the first predetermined area and second predetermined area are of a lesser thickness than the body at all points between the first predetermined area and second predetermined area, wherein both said interior layer and said exterior layer are made of air-impervious material;
open cell foam in said gap space; and
a vent for selectively controlling air flow to said gap space.

10. The interface according to claim 9, wherein a mounting pin hole is disposed through said circular area so as to be centered within said flat circular area.

11. The interface according to claim 9, wherein said vent is disposed in said second predetermined area.

\* \* \* \* \*